US00PP16491P2

(12) United States Plant Patent
Zaiger et al.

(10) Patent No.: US PP16,491 P2
(45) Date of Patent: May 2, 2006

(54) INTERSPECIFIC TREE NAMED: 'FLAVOR ROUGE'

(50) Latin Name: [***Prunus salicina*×(*Prunus Salicina*× *Prunus armeniaca***]
Varietal Denomination: Flavor Rouge

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 190 days.

(21) Appl. No.: 11/005,513

(22) Filed: Dec. 6, 2004

(51) Int. Cl.
*A01H 5/00* (2006.01)

(52) U.S. Cl. ..... Plt./180
(58) Field of Classification Search ..... Plt./180
See application file for complete search history.

*Primary Examiner*—Anne Marie Grunberg

(57) ABSTRACT

A new and distinct variety of interspecific tree [*Prunus salicina*×(*Prunus salicina*×*Prunus armeniaca*)]. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with very good flavor and eating quality.
2. Fruit with a high average Brix of 19.2°.
3. Heavy and regular bearer of fruit.
4. Fruit holding firm on the tree 2 weeks after maturity (shipping ripe).
5. Vigorous, upright tree growth.
6. Fruit with an attractive red skin color.

1 Drawing Sheet

Botanical classification: [*Prunus salicina*×(*Prunus salicina*×*Prunus armeniaca*)].

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum trees, which are known to us, and mentioned herein, 'Queen Rosa' Plum (non-patented) and 'Red Beaut' Plum (U.S. Plant Pat. No. 2,539).

STATEMENT REGARDING FEDERALLY SPONSORED RESEARCH AND DEVELOPMENT

Not applicable.

ORIGIN OF THE VARIETY

The present new variety of interspecific tree [*Prunus salicina*×(*Prunus salicina*×*Prunus armeniaca*)] was originated by us in our experimental orchard located near Modesto, Calif. as an open pollinated seedling selection of the proprietary interspecific seedling with field identification number '293LF464'. The interspecific seedling (293LF464) originated from a cross of 'Queen Rosa' Plum (non-patented) with the proprietary plumcot selection '2G1180'. The plumcot selection (4G1180) (*Prunus salicina*×*Prunus armeniaca*) originated from an open pollinated selection seedling of 'Red Beaut' Plum (U.S. Plant Pat. No. 2,539), which crossed with an apricot of unknown parentage. A large group of these open pollinated seedlings were planted and grown on their own root system. Under close and careful observation, one such seedling, which is the present variety, exhibited desirable fruit characteristics and, in 1996, was selected for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new interspecific tree is of large size, vigorous, upright growth and a productive and regular bearer of small to medium size fruit with very good flavor and eating quality. The fruit is further characterized by having firm flesh, holding firm on the tree 2 weeks after maturity (shipping ripe), being moderately juicy with a good balance between acid and sugar and having good handling and storage quality. In comparison to the parent plum 'Red Beaut' (U.S. Plant Pat. No. 2,539), the new variety is approximately 10 days later in maturity, has a multicolored flesh compared to yellow, has improved flavor with a higher Brix and has a slightly darker skin color. In comparison to 'Queen Rosa' Plum (non-patented), the fruit of the new variety is smaller in size, more round in shape and is approximately 10 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large. Usually pruned to 3 to 3.5 meters in height for economical harvesting of fruit.

*Vigor.*—Vigorous, growth of 1.5 to 2 meters in height the first growing season. Varies with fertility of soil, cultural practices and climatic conditions.

*Form.*—Upright, usually pruned to vase shape.

*Branching habit.*—Upright, crotch angle approximately 30°. Heavy crop load increases crotch angle.

*Productivity.*—Heavy, thinning and spacing of fruit necessary for desired market size.

*Bearer.*—Regular, 4 consecutive years of adequate fruit set. No alternate bearing observed.

*Fertility.*—Self sterile, pollenizer required.

*Density.*—Medium dense. Pruned to vase shape to allow more sunlight and air movement into center of tree to enhance fruit color and health of fruit spurs.

*Hardiness.*—Tree grown in USDA Hardiness Zone 9. Hardy in all stone fruit areas of California. Winter chilling requirement of approximately 500 hours at or below 45° F.

Trunk:

*Size.*—Size — medium. Average circumference 43.1 cm at 20.3 cm from ground on a 6 year old tree.

*Texture.*—Medium shaggy, gets rougher with age.

*Color.*—Varies from 7.5YR 4/2 to 5Y 6/2.

Branches:

*Size.*—Medium to large. Average circumference 18.2 cm at 0.9 meters above ground.

*Surface texture.*—New growth smooth. Mature growth medium rough.

*Lenticels.*—Size — medium. Average length 2.4 mm. Average width 0.9 mm. Average number of 31 in a 25.8 square cm surface of branch. Color varies from 5YR 5/8 to 7.5YR 5/8.

*Color.*—New growth varies from 5GY 6/8 to 5Y 4/6. Mature growth varies from 10YR 4/6 to 2.5YR 4/4, varies with age of growth.

Leaves:

*Size.*—Medium to large. Average length 101.1 mm. Average width 46.3 mm.

*Form.*—Oblanceolate.

*Apex.*—Acuminate.

*Base.*—Cunate.

*Margin.*—Doubly serrate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Average length 11.7 mm. Average width 1.4 mm. Longitudinally grooved. Surface — glabrous. Color varies from 5GY 7/6 to 5GY 6/6.

*Glands.*—Reniform. Size — small to medium. Average length 0.9 mm. Average width 0.6 mm. Average number 3, varies from 2 to 4. Located on base of leaf blade and upper portion of petiole. Color varies from 2.5GY 6/4 to 5GY 6/4.

*Color.*—Upper surface varies from 5GY 3/6 to 7.5GY 3/6. Lower surface varies from 5GY 4/4 to 7.5GY 4/4. Midvein color varies from 5GY 5/4 to 7.5GY 6/4.

Flower buds:

*Size.*—Medium. Average length 10.8 mm. Average diameter 6.6 mm.

*Hardiness.*—Hardy in all stone fruit growing areas of California.

*Form.*—Conical, becomes slightly elongated just before opening.

*Pedicel.*—Long in length, thin in width, glabrous. Average length 11.4 mm. Average width 0.6 mm. Color varies from 2.5GY 8/6 to 2.5GY 8/8.

*Color.*—N 9.5/.

*Number of buds per spur.*—Average 3, varies from 1 to 6.

Flowers:

*Size.*—Medium. Average height 10.3 mm. Average diameter 21.3 mm.

*Petals.*—Number — 5, alternately arranged to sepals. Size — medium. Average length 12.1 mm. Average width 9.0 mm. Shape — obovate, narrows at point of attachment. Margin — sinuate. Color N 9.5/.

*Sepals.*—Number — 5, alternately arranged to petals. Size — small. Average length 4.6 mm. Average width 3.0 mm. Margin — entire. Shape — triangular, slightly rounded apex. Color — upper surfaces varies from 2.5GY 6/8 to 5GY 7/8. Lower surface varies from 2.5GY 6/8 to 5GY 7/10. Both surfaces glabrous.

*Stamens.*—Average number per flower 32. Average filament length 6.0 mm. Filament color N 9.5/. Anther color varies from 2.5Y 7/2 to 5Y 8/10.

*Pollen.*—Self sterile, pollenizer required. Color varies from 2.5Y 7/12 to 5Y 7/8.

*Pistil.*—Normally one. Average length 9.5 mm. Surface glabrous. Stigma height even with anthers. Color varies from 10Y 8/8 to 2.5GY 8/6.

*Fragrance.*—Moderate aroma.

*Blooming period.*—Date of First Bloom Feb. 20, 2004. Date of Petal Fall Feb. 28, 2004. Varies slightly with climatic conditions.

*Color.*—N 9.5/.

*Number flowers per flower bud.*—Usually 2, varies from 1 to 3.

*Pedicel.*—Average length 13.2 mm. Average width 0.7 mm. Color varies from 2.5GY 7/6 to 2.5GY 7/8.

Fruit:

*Maturity when described.*—Firm ripe.

*Date of first picking.*—Jun. 10, 2004.

*Date of last picking.*—Jun. 15, 2004, varies slightly with climatic conditions.

*Size.*—Small to medium. Average diameter axially 47.9 mm. Average transversely in suture plane 47.7 mm. Average weight 67.2 grams, varies slightly with fertility of the soil, amount of thinning and climatic conditions.

*Form.*—Globose.

*Suture.*—Nearly smooth, extends from base to apex.

*Ventral surface.*—Nearly smooth.

*Apex.*—Very slightly enlarged, slight projection.

*Base.*—Nearly flat, slightly refuse.

*Cavity.*—Rounded to slightly elongated in suture plane. Average depth 8.4 mm. Average diameter 12.2 mm.

Stem:

*Size.*—Long and slender. Average length 17.8 mm. Average diameter 1.7 mm.

*Color.*—Varies from 2.5Y 5/6 to 2.5Y 5/8.

Flesh:

*Ripens.*—Slightly earlier near skin surface.

*Texture.*—Firm, meaty.

*Fibers.*—Moderate amount, small, tender.

*Firmness.*—Firm, similar to firmness of 'Red Beaut' Plum (U.S. Plant Pat. No. 2,539).

*Aroma.*—Moderate.

*Amydgalin.*—Undetected.

*Eating quality.*—Very good.

*Flavor.*—Very good, good balance between acid and sugar.

*Juice.*—Moderate, enhances flavor.

*Brix.*—Average 19.2°, varies slightly with amount of fruit per tree and climatic conditions.

*Color.*—Varies from 2.5Y 8/6 near stone to 7.5R 3/10 near skin surface. Pit cavity varies from 10YR 4/6 to 10YR 5/6.

Skin:

*Thickness.*—Medium.

*Surface.*—Smooth.

*Bloom.*—Moderate, complete coverage.

*Tendency to crack.*—Slight.

*Color.*—Ground color varies from 2.5Y 7/6 to 2.5Y 8/6. Overspread with 5R 3/6 to 5R 3/8. Very small, randomly spaced area of ground color showing to skin surface giving a speckling pattern.

*Tenacity.*—Tenacious to flesh.

*Astringency.*—Undetected.

Stone:

*Type.*—Clingstone.

*Size.*—Small. Average length 21.7 mm. Average width 16.9 mm. Average thickness 9.8 mm.

*Form.*—Ovoid.

*Base.*—Relatively flat, some stones slightly pointed.

*Apex.*—Slightly pointed. Average length 0.9 mm.

*Surface.*—Slightly pitted throughout, one small, narrow groove on each side of suture.

*Sides.*—Unequal, one side extending further from suture plane.

*Ridges.*—Several small, short, narrow ridges extending from base toward apex.

*Tendency to split.*—None.

*Color.*—Varies from 7.5YR 6/4 to 7.5YR 5/6 when dry.

Kernal:

*Size.*—Small. Average length 12.6 mm. Average width 8.9 mm. Average thickness 4.6 mm.

*Form.*—Ovate.

*Viability.*—Viable, embryo developed.

*Skin color.*—Varies from 5Y 9/4 to 5Y 9/6 when dry.

Use: Dessert. Market — local and long distance.

Keeping quality: Good, held firm in cold storage 2 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth and being a productive and regular bearer of small to medium size, clingstone fruit with very good flavor and eating quality; the fruit is further characterized by having firm flesh, holding firm on the tree 2 weeks after maturity (shipping ripe), and in comparison to the 'Red Beaut' Plum, the new variety has multicolored flesh compared to yellow and is approximately 10 days later in maturity.

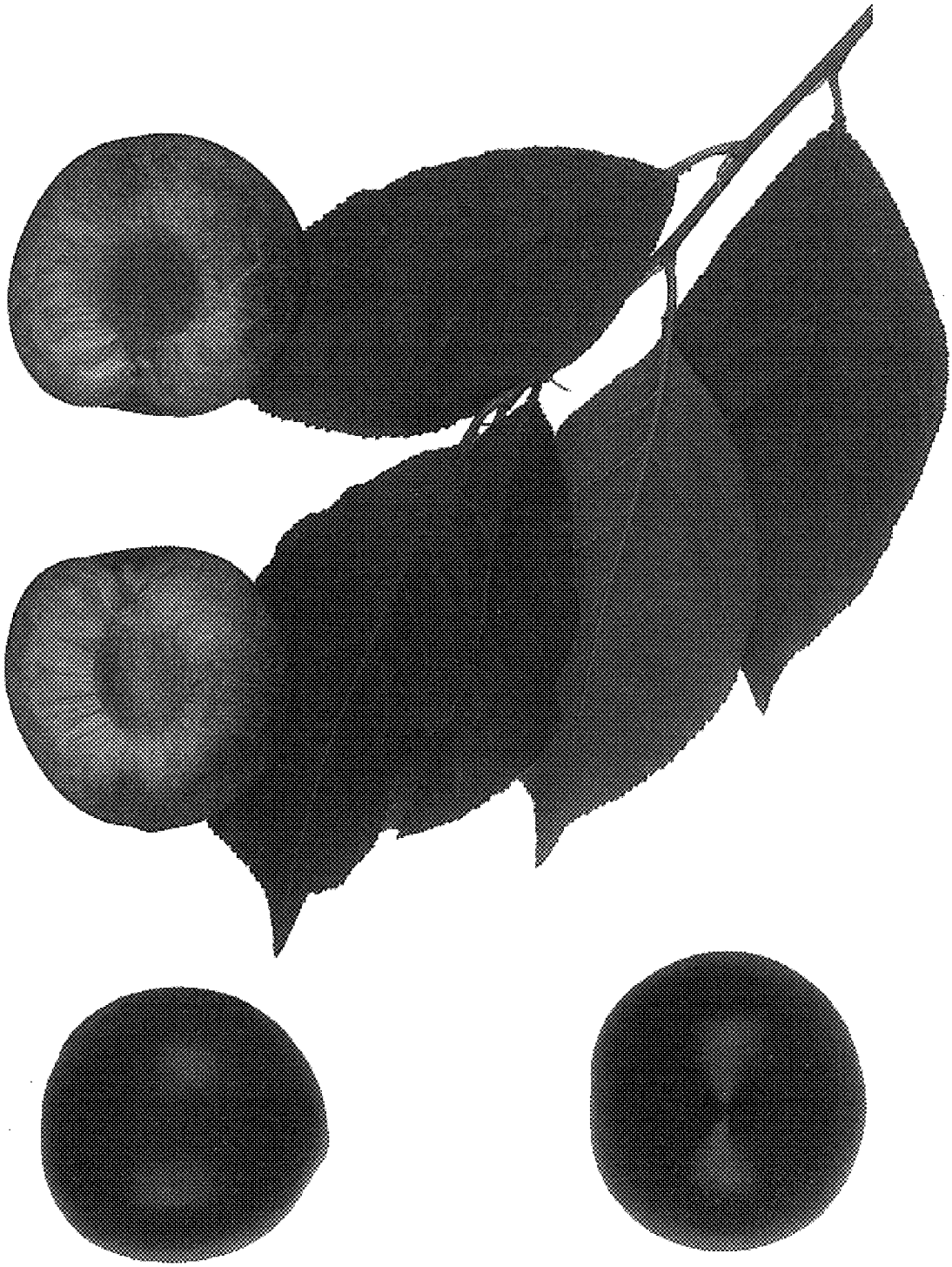

* * * * *